United States Patent
Shirasu-Hiza et al.

(10) Patent No.: US 11,116,754 B2
(45) Date of Patent: Sep. 14, 2021

(54) INHIBITION OF TOR COMPLEX 2 INCREASES IMMUNITY AGAINST BACTERIAL INFECTION

(71) Applicant: THE TRUSTEES OF COLUMBIA UNIVERSITY IN THE CITY OF NEW YORK, New York, NY (US)

(72) Inventors: Michele Shirasu-Hiza, New York, NY (US); Julie Canman, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 441 days.

(21) Appl. No.: 15/774,403

(22) PCT Filed: Nov. 14, 2016

(86) PCT No.: PCT/US2016/061867
§ 371 (c)(1),
(2) Date: May 8, 2018

(87) PCT Pub. No.: WO2017/083835
PCT Pub. Date: May 18, 2017

(65) Prior Publication Data
US 2020/0281902 A1    Sep. 10, 2020

Related U.S. Application Data

(60) Provisional application No. 62/254,957, filed on Nov. 13, 2015.

(51) Int. Cl.
| | |
|---|---|
| *A61K 31/436* | (2006.01) |
| *A61P 31/04* | (2006.01) |
| *A61K 31/4745* | (2006.01) |
| *A61K 31/519* | (2006.01) |
| *A61K 31/7105* | (2006.01) |
| *A61K 31/715* | (2006.01) |

(52) U.S. Cl.
CPC ........ *A61K 31/436* (2013.01); *A61K 31/4745* (2013.01); *A61K 31/519* (2013.01); *A61K 31/715* (2013.01); *A61K 31/7105* (2013.01); *A61P 31/04* (2018.01)

(58) Field of Classification Search
CPC .............. A61K 31/436; A61K 31/4745; A61K 31/519; A61K 31/7088; A61K 31/7105; A61K 31/715; A61P 31/04; A61P 31/20; C12N 15/113
See application file for complete search history.

(56) References Cited

U.S. PATENT DOCUMENTS

| 6,555,328 | B1 | 4/2003 | Keesler et al. |
| 2011/0021551 | A1 | 1/2011 | Moss et al. |
| 2011/0129496 | A1 | 6/2011 | Ahmed et al. |
| 2011/0178070 | A1 | 7/2011 | Gong et al. |
| 2012/0190676 | A1 | 7/2012 | Moorman et al. |
| 2013/0323284 | A1 | 12/2013 | Alonso et al. |
| 2014/0336159 | A1 | 11/2014 | Clarke et al. |
| 2015/0284459 | A1 | 10/2015 | Kuchroo et al. |

FOREIGN PATENT DOCUMENTS

WO    WO 2014/176281    10/2014

OTHER PUBLICATIONS

ScienceNews (Science Daily, https://www.sciencedaily.com/releases /2012/04/120422162413.htm, 2012) (Year: 2012).*
Abdulrahman (Autophagy, 7:11, 1359-70, Nov. 2011) (Year: 2011).*
Liu et al. (The JBC, 287, 13, 9742-52, 2012). (Year: 2012).*
Petersen, Clinical Microbiology and Infection 24 (2018) 369-375 (Year: 2018).*
Doron, Bacterial Infections: Overview, 2008 (Year: 2008).*
Hayat, Medimoon, 2014 (Year: 2014).*
Lee et al. (Apr. 15, 2009) "Rapamycin weekly maintenance dosing and the potential efficacy of combination sorafenib plus rapamycin but not atorvastatin or doxycycline in tuberous sclerosis preclinical models". BMC Pharmacol. 9:8.
Ikai et al. (Oct. 20, 2011). "The reverse, but coordinated, roles of Tor2 (TORC1) and Tor1 (TORC2) kinases for growth, cell cycle and separase-mediated mitosis in Schizosaccharomyces pombe". Open Biol. 1:110007.
Brown et al. (Dec. 30, 2011). "Mammalian Target of Rapamycin Complex 2 (mTORC2) Negatively Regulates Toll-like Receptor 4-mediated Inflammatory Response via FoxO1". Journal of Biological Chemistry 286:44295-44305.
Ayres et al. (Mar. 2008). Identification of *Drosophila* mutants altering defense of and endurance to Listeria monocytogenes infection. Genetics 178:1807-1815.
Huang and Manning (Jun. 1, 2008). The TSC1-TSC2 complex: a molecular switchboard controlling cell growth. *Biochemical Journal* 412:179-190.
Khapre et al. (Aug. 2014). Metabolic clock generates nutrient anticipation rhythms in mTOR signaling. *Aging* 6:675-689.
Krishnan et al. (Jul. 15, 2008). Circadian regulation of response to oxidative stress in *Drosophila melanogaster*. Biochem Biophys Res Commun 374:299-303.

(Continued)

*Primary Examiner* — Umamaheswari Ramachandran
(74) *Attorney, Agent, or Firm* — Leason Ellis LLP

(57) ABSTRACT

This invention relates to methods and compositions for increasing immunity against, and survival of, a bacterial infection by inhibiting Target of Rapamycin (TOR) complex 2 or TORC 2. In particular, the current invention is useful in increasing immunity and survival after infection by *Burkholderia cepacia* as well as other bacteria since the agents that target TORC2 increase host tolerance of infection rather than target the clearance or containment of specific types of bacteria. This invention also relates to methods and compositions for increasing immunity against, survival of, and host tolerance to a bacterial infection by inhibiting the circadian regulator, Period protein.

4 Claims, 7 Drawing Sheets

Specification includes a Sequence Listing.

(56) References Cited

OTHER PUBLICATIONS

Lowrey and Takahashi. (2004). Mammalian circadian biology: elucidating genome-wide levels of temporal organization. *Annu. Rev. Genomics Hum. Genet.* 5:407-441. Available in PMC Sep. 11, 2013.

Martin and Mohr. (Jan. 2000). Invasion and intracellular survival of *Burkholderia cepacia*. *Infect. Immun.* 68:24-29.

Schneider and Ayres. (Nov. 1, 2008). Two ways to survive infection: what resistance and tolerance can teach us about treating infectious diseases. *Nat. Rev. Immunol.* 8:889-895.

Schwager et al. (Jan. 2013). Identification of *Burkholderia cenocepacia* Strain H111 Virulence Factors Using Nonmammalian Infection Hosts. *Infection and Immunity* 81:143-153.

Sparks and Guertin. (Apr. 26, 2010) Targeting mTOR; prospects for mTOR complex 2 inhibitors in cancer therapy. *Oncogene* 29:3733-3744.

Thomson et al. (May 2009). Immunoregulatory functions of mTOR inhibition. *Nature Review Immunology* 9:324-337.

Delgoffe et al. "The mammalian Target of Rapamycin (mTOR) regulates T helper cell differentiation through the selective activation of mTORC1 and mTORC2 signaling," Nat Immunol, Feb. 27, 2011 (Feb. 27, 2011). vol. 12. pp. 295-303. entire document.

Stone et al. "The Circadian Clock Protein Timeless Regulates Phagocytosis of Bacteria in *Drosophila*," PLoS Pathogens, Jan. 12, 2012 (Jan. 12, 2012), vol. 8, Iss. 1, e1002445, pp. 1-11. entire document.

Bollinger et al. "Sleep, Immunity, and Circadian Clocks: A Mechanistic Model," Gerontology, Feb. 3, 2010 (Feb. 3, 2010), vol. 56, pp. 574-580. entire document.

Silver et al. "The circadian clock controls toll-like receptor 9-mediated innate and adaptive immunity," Immunity, Feb. 24, 2012 (Feb. 24, 2012), vol. 36, pp. 251-261. entire document.

Liu et al. "The Circadian Clock Period 2 Gene Regulates Gamma Interferon Production or NK Cells in Host Response to Lipopolysaccharide-Induced Endotoxic Shock," Infection and Immunity, Aug. 1, 2006 (Aug. 1, 2006), vol. 74, pp. 4750-4756. entire document.

Pedicord et al. "Friends Not Foes: CTLA-4 Blockade and mTOR Inhibition Cooperate during CD8+ T Cell Priming to Promote Memory Formation and Metabolic Readiness," The Journal of Immunology, Jan. 26, 2015 (Jan. 26, 2015), vol. 194, pp. 2089-2098. entire document.

AlQurashi et al. (Feb. 13, 2013) Chemical Inhibitors and microRNAs (miRNA) Targeting the Mammalian Target of Rapamycin (mTOR) Pathway: Potential for Novel Anticancer Therapeutics. *Int. J. Mol. Sci.* 14:3874-3900.

Ayres and Schneider. (Jul. 14, 2009). The role of anorexia in resistance and tolerance to infections in *Drosophila*. *PLoS Biol* 7:e1000150.

Ayres and Schneider. (Dec. 9, 2008). A signaling protease required for melanization in *Drosophila* affects resistance and tolerance of infections. *PLoS Biol* 6:2764-2773.

Brennan and Anderson. (Apr. 23, 2004). *Drosophila*: the genetics of innate immune recognition and response. *Annual Review of Immunology* 22:457-483.

Castonguay-Vanier et al. (Jul. 12, 2010). *Drosophila melanogaster* as a model host for the *Burkholderia cepacia* complex. *PloS one* 5:e11467.

Cui et al. (Jun. 13, 2016). microRNA-153 targets mTORC2 component Rictor to inhibit glioma cells. *Plos One* 11:e0156915.

D'Argenio et al. (Feb. 2001). *Drosophila* as a model host for *Pseudomonas aeruginosa* infection. *J Bacteriol.* 183:1466-1471.

Delgoffe et al. (Jun. 19, 2009). The mTOR Kinase Differentially Regulates Effector and Regulatory T Cell Lineage Commitment. *Immunity* 30:832-844.

Dimitroff et al. (Feb. 3, 2012). Diet and Energy-Sensing Inputs Affect TorC1-Mediated Axon Misrouting but Not TorC2-Directed Synapse Growth in a *Drosophila* Model of Tuberous Sclerosis. *PloS one* 7:e30722.

Dionne et al. (Oct. 24, 2006). Akt and FOXO dysregulation contribute to infection-induced wasting in *Drosophila*. *Current Biology* 16:1977-1985.

Foldenauer et al. (Apr. 26, 2013) Mammalian target of rapamycin regulates IL-10 and resistance to *Pseudomonas aeruginosa* corneal infection. *J. Immunol.* 190:5649-58.

Green et al. (Sep. 5, 2008). The meter of metabolism. *Cell* 134:728-742.

Hietakangas and Cohen. (Jan. 29, 2007). Re-evaluating AKT regulation: role of TOR complex 2 in tissue growth. *Genes Dev* 21:632-637.

Konopka and Benzer (Sep. 1971). Clock mutants of *Drosophila melanogaster*. *Proc. Natl. Acad. Sci.* 68:2112-2116.

Lee and Edery. (Feb. 12, 2008). Circadian regulation in the ability of *Drosophila* to combat pathogenic infections. *Current Biology* 18:195-199.

Loewith et al. (Sep. 2002). Two TOR complexes, only one of which is rapamycin sensitive, have distinct roles in cell growth control. *Molecular Cell* 10:457-468.

Medzhitov et al. (Feb. 24, 2012). Disease tolerance as a defense strategy. *Science* 335:936-941.

Pham et al. (Mar. 9, 2007). A specific primed immune response in *Drosophila* is dependent on phagocytes. *PLoS Pathog* 3:e26.

Raberg et al. (Nov. 2, 2007). Disentangling genetic variation for resistance and tolerance to infectious diseases in animals. *Science* 318:812-814.

Schneider et al. (Mar. 23, 2007). *Drosophila* eiger mutants are sensitive to extracellular pathogens. *PLoS Pathog.* 3:e41.

Shirasu-Hiza et al. (May 15, 2007). Interactions between circadian rhythm and immunity in *Drosophila melanogaster*. *Current Biology* 17: R353-355.

Stone et al. (Jan. 12, 2012) The circadian clock protein timeless regulates phagocytosis of bacteria in *Drosophila*. *PLoS Pathog* 8:e1002445.

Tapon et al. (May 4, 2001). The *Drosophila* tuberous sclerosis complex gene homologs restrict cell growth and cell proliferation. *Cell* 105, 345-355.

Uesugi et al. (Sep. 1, 2011) The tumor suppressive microRNA miR-218 targets the mTOR component Rictor and inhibits AKT phosphorylation in oral cancer. *Cancer Res.* 71:5765-78.

Xu et al. (Oct. 8, 2008). Regulation of feeding and metabolism by neuronal and peripheral clocks in *Drosophila*. *Cell Metabolism* 8:289-300.

* cited by examiner

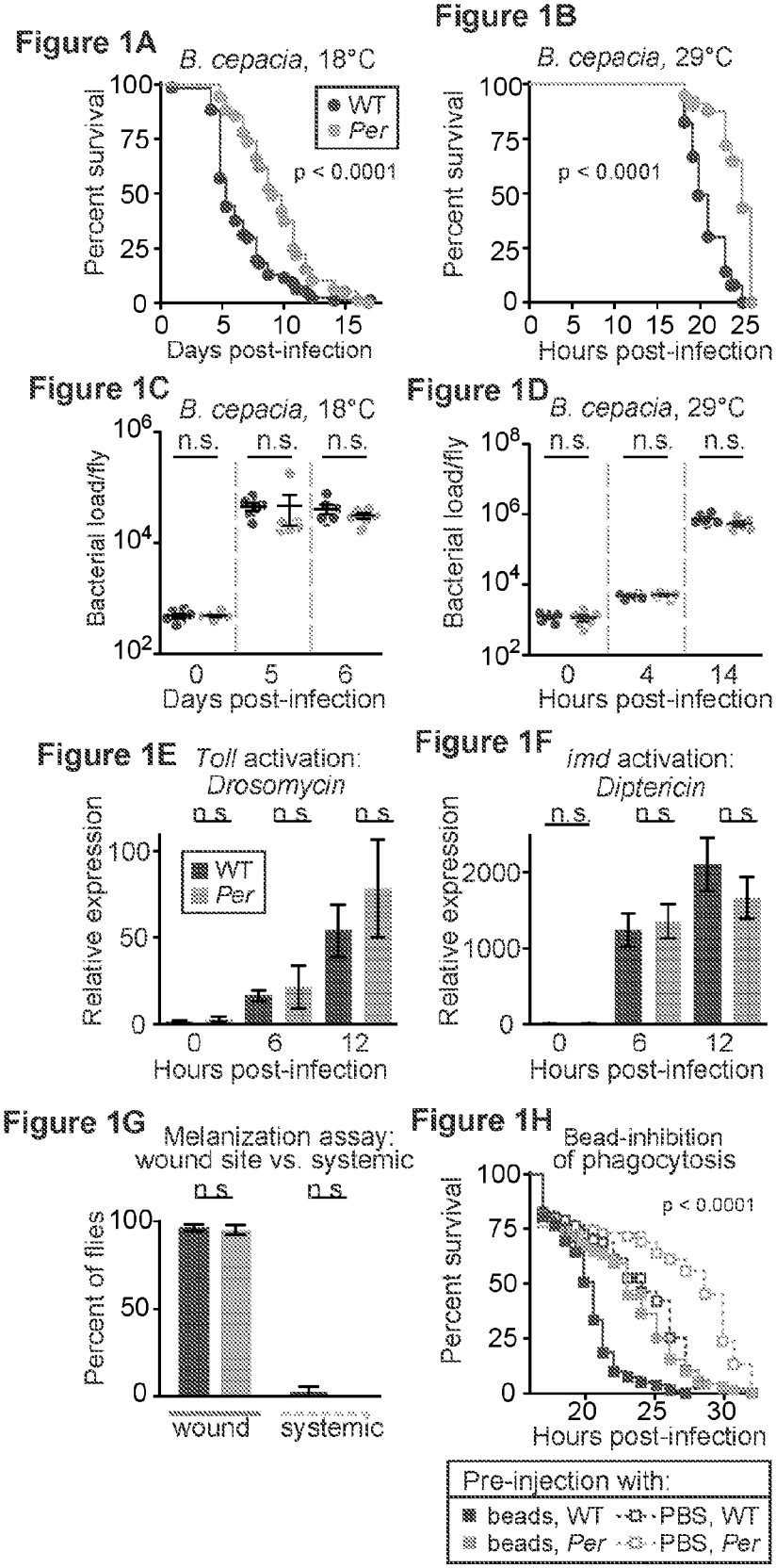

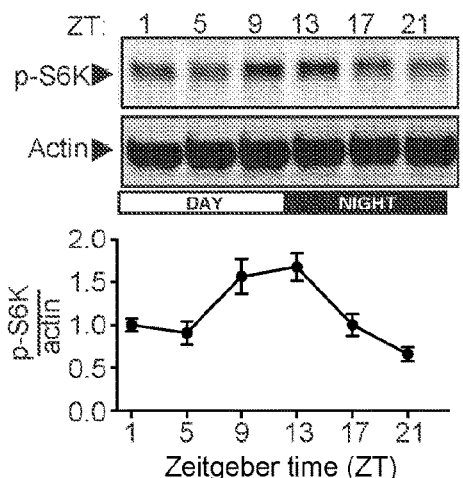
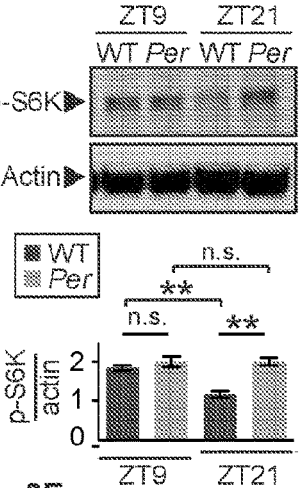
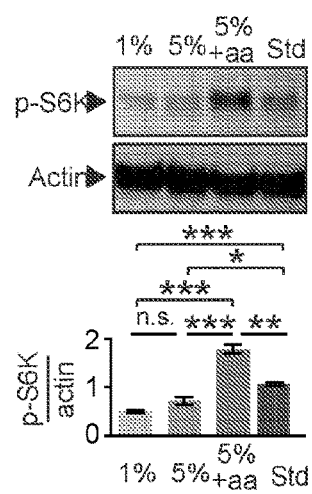
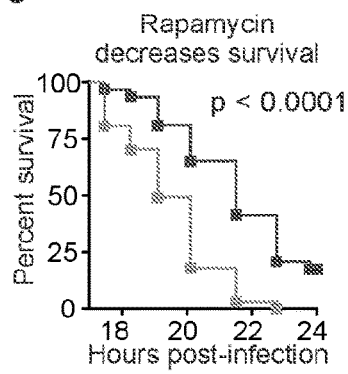
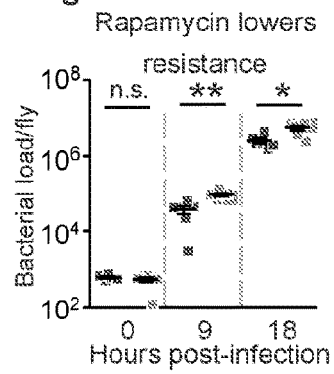
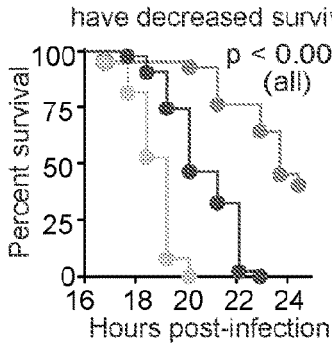
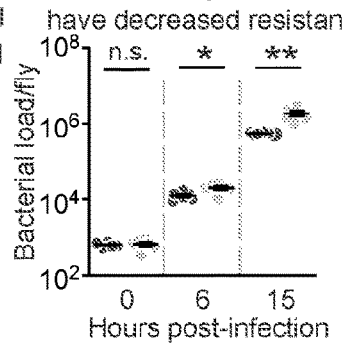

Sin1 mutants -a.a. survive similarly to WT +a.a.

Sin1 mutants -a.a. have similar bacterial loads as WT +a.a.

○ WT 5% glucose + a.a.
● Sin1 5% glucose

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
ccgcagtacc cactcaatc                                              19

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
cccaagtgct gtccatatcc                                             20

<210> SEQ ID NO 3
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 3
ccatcgagga tcacctgact                                                    20

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
ctttaggcgg gcagaatg                                                      18
```

INHIBITION OF TOR COMPLEX 2 INCREASES IMMUNITY AGAINST BACTERIAL INFECTION

CROSS REFERENCE TO RELATED APPLICATION

The present application is a U.S. National Phase Application under 35 U.S.C. § 371 of International Patent Application No. PCT/US2016/061867, filed Nov. 14, 2016, which claims priority to U.S. patent application Ser. No. 62/254,957 filed Nov. 13, 2015, each of which is hereby incorporated by reference as if expressly set forth in their respective entirety herein. The International Application was published in English on May 18, 2017 as WO 2017/083835.

This invention was made with government support under GM105775, OD008773, DK092735 and NS080673, all awarded by NIH. The government has certain rights in the invention.

FIELD OF THE INVENTION

This invention is in the field of immunity and relates to increasing immunity against, and survival of, a bacterial infection in a subject by inhibiting Target of Rapamycin (TOR) complex 2 or TORC 2.

BACKGROUND OF THE INVENTION

Evolutionarily conserved circadian mechanisms regulate daily, dynamic changes in animal behavior and physiology (Lowrey and Takahashi 2004). Circadian oscillations in gene expression are thought to cause circadian oscillations in physiological function and ultimately organismal behavior. It was previously found that *Drosophila* innate immunity against *S. pneumoniae* infection is circadian-regulated (Shirasu-Hiza et al. 2007; Stone et al. 2012). For both flies and vertebrates, innate immunity is the first line of defense against infection. While *Drosophila* lack adaptive immune components such as T cells and B cells and rely on innate immune responses only to survive infection (Brennan and Anderson 2004), flies and vertebrates employ several similar innate immune mechanisms to kill bacteria, including phagocytosis by immune cells, reactive oxygen species generation (melanization in flies), and secretion of antimicrobial peptides (AMPs).

Resistance is only one type of defense against bacterial infection. Resistance mechanisms such as the immune functions listed above control bacterial proliferation, reducing pathogenesis by decreasing the host's pathogen burden. A second distinct, complementary type of defense is termed tolerance (Schneider and Ayres 2008; Medzhitov et al. 2012). Tolerance physiologies allow the organism to survive the pathological effects of infection, caused by microbes or the host immune response, without necessarily decreasing bacterial load (Raberg et al. 2007; Ayres et al. 2008). Tolerance physiologies are not well understood, but include feeding and metabolism. Both feeding behavior and metabolic gene expression are circadian-regulated, and both fly and mouse circadian mutants exhibit metabolic disorders and altered feeding behavior (Xu et al. 2008; Green et al. 2008). While it was shown previously that host resistance against specific pathogens is circadian-regulated, it is not clear whether loss of circadian-regulated metabolism and feeding behavior affect immunity against infection (Shirasu-Hiza et al. 2007; Stone et al. 2012; Lee and Edery 2008).

Target of Rapamycin or TOR associates with two related but distinct complexes, TOR complex 1 (TORC1) and TOR complex 2 (TORC2) which in some contexts have opposite effects (Ikai et al. 2011; Delgoffe et al. 2009). As shown herein, TORC1 activity is circadian-regulated and activates resistance in *Drosophila*, similar to what is observed in vertebrates (Thomson et al. 2009).

In contrast, as shown herein, the less well-characterized TORC2 had the opposite effect on survival and inhibits both resistance and tolerance, in particular in response to infection by *Burkholderia cepacia*, which is responsible for significant opportunistic infections, especially in hospital settings. These systemic bacterial infections, such as sepsis or septicemia, are a significant public health problem, especially in the face of antibiotic-resistant strains. This hospital-acquired infection is associated with high rates of mortality, up to 50% for severe strains, and is often antibiotic-resistant. The tolerance mechanisms increasing survival of this infection are currently unknown. More effective treatments for these infections are needed.

Thus, the inhibition of TORC2 or the circadian regulator Period protein could provide novel therapy survival of infection and for increasing immunity to bacterial infections.

SUMMARY OF THE INVENTION

The present invention is based upon the surprising discovery that inhibition of TOR complex 2 or TORC2 increases survival after infection by bacteria, specifically *Burkholderia cepacia, Pseudomonas aeruginosa*, and other types that cause septicemia. The inhibition of TORC2 increases immunity both through resistance to the bacteria and through tolerance. Because increased tolerance is due to effects on host survival and defense against pathogenesis rather than due to containment or clearance of specific bacteria, therapeutics that increase tolerance are likely to be effective for multiple types of septicemia regardless of source or bacterial species.

One embodiment of the present invention would include a method for increasing survival after an infection caused by a microbe, comprising administering to a subject in need thereof, a therapeutically effective amount of an agent that inhibits TOR complex 2. In a preferred embodiment, the microbe is bacteria, and in a more preferred embodiment the bacteria is *Burkholderia cepacia*. The preferred subject is a mammal and a more preferred subject is a human. In one embodiment, agents that can be used to inhibit TOR complex 2 include but are not limited to small molecules, nucleic acids, proteins, and antibodies. In one embodiment, the agent that inhibits TOR complex 2 is a small molecule. Small molecules include but are not limited to pyridinon-equinolines, pyrazolopyrimidines, and pyridopyrimidines. In a further embodiment, the agent is Torin. In a further embodiment, the nucleic acid includes but is not limited to antisense oligonucleotide, siRNA, shRNA, and combinations thereof. In a further embodiment, the agent that inhibits TOR complex 2 would not inhibit TOR complex 1. In one embodiment, the infection is septicemia. In one embodiment, the infection is sepsis.

One embodiment of the present invention is a method of treating or preventing an infection caused by a microbe, comprising administering to a subject in need thereof a therapeutically effective amount of an agent that inhibits TOR complex 2. In a preferred embodiment, the microbe is bacteria, and in a more preferred embodiment the bacteria is *Burkholderia cepacia*. The preferred subject is a mammal and a more preferred subject is a human. In one embodiment, agents that can be used to inhibit TOR complex 2 include but are not limited to small molecules, nucleic acids, proteins, and antibodies. In one embodiment, the agent that inhibits TOR complex 2 is a small molecule. Small molecules include but are not limited to pyridinonequinolines, pyrazolopyrimidines, and pyridopyrimidines. In a further embodiment, the agent is Torin. In a further embodiment, the nucleic acid includes but is not limited to antisense oligonucleotide, siRNA, shRNA, and combinations thereof. In a further embodiment, the agent that inhibits TOR complex 2 would not inhibit TOR complex 1. In one embodiment, the infection is septicemia. In one embodiment, the infection is sepsis A further embodiment of the present invention is a method for increasing immunity to an infection caused by microbe, comprising administering to a subject in need thereof a therapeutically effective amount of an agent that inhibits TOR complex 2. In a preferred embodiment, the microbe is bacteria, and in a more preferred embodiment the bacteria is *Burkholderia cepacia*. The preferred subject is a mammal and a more preferred subject is a human. In one embodiment, agents that can be used to inhibit TOR complex 2 include but are not limited to small molecules, nucleic acids, proteins, and antibodies. In one embodiment, the agent that inhibits TOR complex 2 is a small molecule. Small molecules include but are not limited to pyridinonequinolines, pyrazolopyrimidines, and pyridopyrimidines. In a further embodiment, the agent is Torin. In a further embodiment, the nucleic acid includes but is not limited to antisense oligonucleotide, siRNA, shRNA, and combinations thereof. In a further embodiment, the agent that inhibits TOR complex 2 would not inhibit TOR complex 1. In one embodiment, the infection is septicemia. In one embodiment, the infection is sepsis Yet a further embodiment of the present invention is a method for increasing tolerance to an infection caused by a microbe, comprising administering to a subject in need thereof a therapeutically effective amount of an agent that inhibits TOR complex 2. In a preferred embodiment, the microbe is bacteria, and in a more preferred embodiment the bacteria is *Burkholderia cepacia*. The preferred subject is a mammal and a more preferred subject is a human. In one embodiment, agents that can be used to inhibit TOR complex 2 include but are not limited to small molecules, nucleic acids, proteins, and antibodies. In one embodiment, the agent that inhibits TOR complex 2 is a small molecule. Small molecules include but are not limited to pyridinonequinolines, pyrazolopyrimidines, and pyridopyrimidines. In a further embodiment, the agent is Torin. In a further embodiment, the nucleic acid includes but is not limited to antisense oligonucleotide, siRNA, shRNA, and combinations thereof. In a further embodiment, the agent that inhibits TOR complex 2 would not inhibit TOR complex 1. In one embodiment, the infection is septicemia. In one embodiment, the infection is sepsis Yet a further embodiment of the present invention is a method for increasing resistance to an infection caused by a microbe, comprising administering to a subject in need thereof a therapeutically effective amount of an agent that inhibits TOR complex 2. In a preferred embodiment, the microbe is bacteria, and in a more preferred embodiment the bacteria is *Burkholderia cepacia*. The preferred subject is a mammal and a more preferred subject is a human. In one embodiment, agents that can be used to inhibit TOR complex 2 include but are not limited to small molecules, nucleic acids, proteins, and antibodies. In one embodiment, the agent that inhibits TOR complex 2 is a small molecule. Small molecules include but are not limited to pyridinonequinolines, pyrazolopyrimidines, and pyridopyrimidines. In a further embodiment, the agent is Torin. In a further embodiment, the nucleic acid includes but is not limited to antisense oligonucleotide, siRNA, shRNA, and combinations thereof. In a further embodiment, the agent that inhibits TOR complex 2 would not inhibit TOR complex 1. In one embodiment, the infection is septicemia. In one embodiment, the infection is sepsis As shown herein, circadian mutants, such as those with mutations in Per, have increased survival after an infection by a bacteria and that the survival is due to increased host tolerance. See Example 2. The inhibition of Per increases immunity through tolerance. Because increased tolerance is due to effects on host survival and defense against pathogenesis rather than due to containment or clearance of specific bacteria, therapeutics that increase tolerance are likely to be effective for multiple types of septicemia or sepsis regardless of source or bacterial species.

Thus, a further embodiment of the present invention would include a method for increasing survival after an infection caused by a microbe, comprising administering to a subject in need thereof, a therapeutically effective amount of an agent that inhibits Period protein Per. Yet another embodiment of the present invention is a method of treating or preventing an infection caused by a microbe, comprising administering to a subject in need thereof, a therapeutically effective amount of an agent that inhibits Per. A further embodiment of the present invention is a method of increasing immunity to an infection caused by a microbe comprising, administering to a subject in need thereof, a therapeutically effective amount of an agent that inhibits Per. Another embodiment of the present invention would be a method of increasing tolerance to an infection caused by a microbe, comprising administering to a subject in need thereof, a therapeutically effective amount of an agent that inhibits Per.

In all of these embodiments, the microbe can be bacteria, and in a more preferred embodiment the bacteria is *Burkholderia cepacia*. The preferred subject is a mammal and a more preferred subject is a human. In one embodiment, agents that can be used to inhibit Per include but are not limited to small molecules, nucleic acids, proteins, and antibodies. In some embodiments, the infection is septicemia. In one embodiment, the infection is sepsis

BRIEF DESCRIPTION OF THE FIGURES

FIG. 1 shows the results showing that period (per$^{01}$) mutants exhibit greater tolerance than wild type (WT) controls during infection with *Burkholderia cepacia*. FIG. 1A shows the percent survival of per$^{01}$ mutants (light circles) and wild type (dark circles) during a long infection (low dose at low temperature, 18° C.; per01, n=78; WT, n=77, p<0.0001) with *B. cepacia*. FIG. 1B shows the percent survival of per$^{01}$ mutants (light circles) and wild type (dark circles) during a short infection (high dose at high temperature, 29° C.; per$^{01}$, n=57; WT, n=64, p<0.0001) with *B. cepacia*. FIG. 1C shows bacterial load comparisons of per$^{01}$ mutants and wild type flies over time following a long infection (n≥4 flies/time point, all n.s.) and FIG. 1D shows bacterial load comparisons of per$^{01}$ mutants and wild type flies over time following short infection (n=6 flies/time point, all n.s.) with *B. cepacia*. FIG. 1E and FIG. 1F show antimicrobial peptide (AMP) induction via the Toll (Drosomycin) (FIG. 1E) and imd (Diptericin) (FIG. 1F) pathways in per$^{01}$ mutants and wild type flies after *B. cepacia* infection (n=3 samples of 6 flies each, all n.s.). FIG.

1G shows systemic and injection wound site melanization after B. cepacia infection (3 trials, n=17-22 flies/trial/genotype, all n.s.). In FIGS. 1E, 1F and 1G, per$^{01}$ mutants are represented by the light colored bars and wild type flies by the dark colored bars. FIG. 1H shows the results of bead-inhibition of phagocytosis by bead pre-injection in per$^{01}$ mutant and wild type after B. cepacia infection (per$^{01}$, n=76 with beads, n=81 with buffer; wild type, n=81 with beads, n=80 with buffer; p<0.0001 for all pair-wise curve comparisons except WT buffer vs. per$^{01}$ with beads, n.s.). p-values for survival curve comparisons were obtained by log-rank analysis; p-values for bacterial load comparisons were obtained using unpaired t tests for 0 hour time points, while subsequent time points were tested with non-parametric Mann-Whitney U tests; p-values for AMP and melanization comparisons were obtained using unpaired t tests.

FIG. 2 shows that glucose and amino acids increase tolerance of B. cepacia infection in wild type flies.

FIG. 3 shows that TORC1 signaling is circadian-regulated and increases resistance to infection. FIG. 3A contains Western blot analysis (top panel) and quantification (lower panel) of wild type flies, showing that phospho-S6K levels oscillate over the circadian cycle with a peak in the evening and trough in the morning. FIG. 3B shows levels of phospho-S6K at ZT21 and ZT9 for per$^{01}$ mutants and wild type, as determined by Western blot analysis (n=10, ZT21 p=0.0027, ZT9 n.s.) (upper panel is the blot and lower panel is the quantification of the blot). Wild type flies exhibited reduced levels of phospho-S6K at ZT21 compared to ZT9 (n=10, p=0.0026). per$^{01}$ mutants did not show this difference (n.s.). FIG. 3C shows Western blot analysis of levels of phospho-S6K in wild type flies administered 1% glucose, 5% glucose, 5% glucose plus amino acids, and standard diet. (n=10, p<0.0163 for all comparisons except 1% glucose vs. 5% glucose, n.s.) (upper panel is the blot and lower panel is the quantification). FIG. 3D show percent survival of wild type flies co-injected with rapamycin versus buffer at the time of infection. (n=70, p<0.0001). FIG. 3E shows bacterial load of wild type flies co-injected with rapamycin versus buffer at the time of infection (n=6, 0 hrs n.s., 9 hrs p=0.0049, 18 hrs p=0.0198). FIG. 3F shows percent survival of Tsc1/2 overexpression mutant flies infected with B. cepacia. Tsc1 and 2 form a complex that inhibits TORC1. Tsc1/2 overexpression mutants (n=38) exhibit decreased survival time relative to flies containing the driver alone (n=42, p<0.0001) or the construct alone (n=43, p<0.0001). FIG. 3G shows the bacterial load of Tsc1/2 overexpression mutant flies (n=6 for both mutant and construct alone, 0 hrs n.s., 6 hrs p=0.0367, 15 hrs p=0.0022).

FIG. 4 shows the results showing that TORC2 activity decreases both resistance and tolerance of infection. Rictor and Sin1 are two components of TORC2. In FIGS. 4A-4D, all flies were fed 5% glucose plus amino acids.

FIG. 5 shows the results that a known TORC2 inhibitor significantly increases survival after infection.

DETAILED DESCRIPTION OF THE INVENTION

Figure 2A:
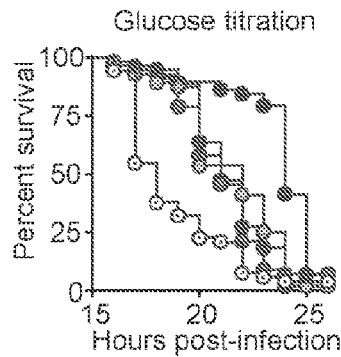
FIG. 2A shows percent survival of infected wild type flies fed various glucose concentration (5%, 10%, or 15%) relative to 1% glucose diet (n>53, p<0.0001 in all cases); higher doses of glucose (5-10%) caused similar survival kinetics compared to each other (n>55, n.s. in all cases), increased survival relative to 1% glucose (p<0.0001 for each), and decreased survival relative to standard food (n=58) (p<0.0001 for all).

The current invention includes methods and compositions for increasing survival and immunity to an infection by a microbe by inhibiting Target of Rapamycin complex 2 or TORC2. The current invention also includes methods and compositions for increasing survival and immunity to an infection by a microbe by inhibiting the circadian regulator, Period protein.

Definitions

The term "subject" as used in this application means an animal with an immune system such as avians and mammals Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

A therapeutically effective amount, or an effective amount, of a drug is an amount effective to demonstrate a desired activity of the drug. A "therapeutically effective amount" will vary depending on the compound, the disorder and its severity and the age, weight, physical condition and responsiveness of the subject to be treated. In certain embodiments, a "therapeutically effective amount of an agent" is used herein to mean an amount sufficient to cause an improvement in a clinically significant condition in the subject, or delays or minimizes or mitigates one or more symptoms associated with the disease, or results in a desired beneficial change of physiology in the subject.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "in need thereof" would be a subject known or suspected of having or being at risk of developing a bacterial infection in particular an infection by *Burkholderia cepacia*. Subjects in particular at risk for a bacterial infection of this type would be those that are immunocompromised, especially as related to the respiratory tract, such as those with cystic fibrosis. Other subjects at risk for a bacterial infection of this type would be those that are in a hospital or nursing home setting.

A subject in need of treatment would be one that has already been diagnosed with an infection. A subject in need of prevention would be one with a risk of developing an infection.

The term "agent" as used herein means a substance that produces or is capable of producing an effect and would include, but is not limited to, chemicals, pharmaceuticals, biologics, small organic molecules, antibodies, nucleic acids, peptides, and proteins.

The term "resistance" as used herein means one type of defense against bacterial infection, and includes mechanisms and immune functions that control bacterial proliferation, by reducing pathogenesis by decreasing the host's pathogen burden.

The term "tolerance" as used herein means a second distinct, complementary type of defense that includes mechanisms to allow the organism to survive the pathological effects of infection, either caused by microbes or the host immune response, without necessarily decreasing bacterial load.

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) *Current Protocols in Molecular Biology, Vols. 1-4*, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Novel Role of TOR Signaling in Innate Immunity Against Bacterial Infection

By examining a circadian mutant $per^{01}$ with increased infection tolerance against *B. cepacia*, it was identified that increased feeding as a circadian-regulated behavior contributes to increased tolerance. Increased feeding by $per^{01}$ mutants was not associated with increased energy stores, suggesting that their increased tolerance does not depend on metabolic reserves. Two specific nutrients, glucose and amino acids, fully substitute for standard food in promoting optimal tolerance after *B. cepacia* infection. The data also suggested a narrow window for glucose's contribution to survival—with this rapid infection, an increase in circulating glucose in the two hours before infection can increase overall survival time. This is consistent with the hypothesis that nutrient sensing leads to an acute activation of infection tolerance. See Examples 2 and 3.

To further explore the effects of dietary amino acids on survival of infection, the role of Target of Rapamycin or TOR complex 1 (TORC1) signaling, a canonical amino acid sensing pathway, was investigated and it was found that TORC1 kinase activity oscillates with circadian rhythm, likely through circadian-regulated feeding behavior as seen in vertebrates (Khapre et al. 2014). A role for TORC1 was uncovered in resistance against infection in *Drosophila*. In vertebrates, TORC1 is known to mediate resistance and rapamycin is a well characterized immunosuppressant; however, these immunosuppressive effects are thought to result primarily from inhibiting the growth and maturation of dendritic cells and T-cells (Thomson et al. 2009), adaptive immune cell types with no clear functional analogs in *Drosophila*. See Examples 4 and 5.

More importantly, a novel role for the less well-known TOR complex 2 (TORC2) as a potent inhibitor of immunity was found. The results suggest that TORC2 is circadian-regulated and that manipulation of circadian regulation or direct inhibition of TORC2 significantly increases the host organism's survival of bacterial infection (up to 59% longer after a lethal infective dose).

The loss of TORC2-specific components Rictor or Sin1 caused dramatic increases in survival time after infection and impacted both resistance and tolerance. Loss of Sin1 increased resistance in the presence of amino acids and increased tolerance in the absence of amino acids. See Example 6.

The finding that TORC2 inhibition increases survival of infection is surprising but not completely without precedent. While most immune effects of TOR are thought to act through TORC1, recent evidence suggests that, in mouse embryonic fibroblasts, Rictor inhibits Toll-like receptor-stimulated cytokine expression (Brown et al. 2011). Thus Rictor may have conserved immune-suppressive effects in both vertebrates and invertebrates.

The cellular and molecular mechanisms that promote host tolerance of infection are not well-understood. *B. cepacia* is a significant opportunistic bacterial pathogen, particularly in hospital settings. As shown herein TORC2 has been identified as a pharmacological target to increase host survival time after infection, as TORC2 mutants were able to survive infection up to 59% longer than wild type (Example 6) and flies administered a TORC2 inhibitor had a significant increase in survival after infection (Example 7). TORC1 inhibitors such as rapamycin are well known and employed to suppress immune system function. In contrast, the potential therapeutic value of TORC2 inhibition has not been explored, as there are currently no available small molecule inhibitors specific to TORC2 and not TORC1.

TOR Complex 2

Mammalian TORC2 consists of a complex that includes mTOR, Rictor (rapamycin-insensitive companion of mTOR) and mSIN1 (mammalian stress-activated protein kinase interacting protein, also known as MAPKAP1). Rictor plays an important role in the phosphorylation of Akt. PROTOR1 (protein observed with Rictor-1) appears to help complex assembly. Rictor, mSIN1 and PROTOR1 proteins are unique components of TORC2, whereas the other known TORC2 accessory proteins, including mLST8 and Deptor, are shared components with mTORC1. However, unlike mTORC1, mLST8 is essential for mTORC2 function, as deletion of this protein can severely reduce the stability and function of this complex. Similar to its role in mTORC1, Deptor acts as a negative regulator of mTORC2. See generally AlQurashi et al. 2013.

As shown in Example 6, *Drosophila* lacking Rictor and Sin1 both had increased survival after infection. Thus, either of these proteins, as well as PROTOR1 can be targeted to inhibit TORC2.

TOR Complex 2 Inhibition

As shown herein, inhibition of TOR complex 2 or TORC2 greatly increases immunity and survival after infection by bacteria, in particular *Burkholderia cepacia*, which causes sepsis in humans and is a major public health issue in hospital settings. Thus, one embodiment of the present invention is a method of increasing immunity and survival after infection in a subject by administering to the subject a therapeutically effective amount of an agent that inhibits TORC2. The agent can inhibit TORC2 only or inhibit both TORC1 and TORC2. Agents for TORC2 inhibition for use in the current invention includes those known now and those developed in the future.

One preferred agent for TORC2 inhibition is small molecules. To date there are no small molecules that inhibit only TORC2. There are small molecules capable of inhibiting TORC2 but they are not specific to TORC2 alone.

The first category of these inhibitors are ATP-competitive inhibitors otherwise known as TORC kinase inhibitors or TKIs (Sparks and Guertin 2010). These small molecules include but are not limited to pyridinonequinolines, pyrazolopyrimidines, and pyridopyrimidines. Several of these types of TORC1/TORC2 inhibitors have been developed and tested and include but are not limited to the small molecules listed in Table 1. All of these small molecules have good selectivity toward TOR, with IC50 values in the low nanomolar range.

TABLE 1

TKI TORC1/TORC2 Inhibitors

| NAME | TYPE |
| --- | --- |
| Torin 1 and 2 | Pyridinonequinoline |
| Torkinib (PP242) | Pyrazolopyrimidine |
| PP30 | Pyrazolopyrimidine |
| Ku-0063794 | Pyrazolopyrimidine |
| WAY-600, WYE-687, WYE-354 | Pyrazolopyrimidine |
| AZD8055 | Pyridopyrimidine |
| INK128 (MLN0128) | |
| OSI-027 | |
| AZD2014 | |
| Omipalisib (GSK2126458, GSK458) | |

Another class of dual specificity inhibitors targets the structurally related kinase domains of both P13K and TORC. These agents include wortmanin, LY294002, PI-103, BGT226, XL765, and NVP-BEZ235 (Sparks and Guertin 2010).

All of these small molecules are in development and/or clinical trials, and can be obtained from Selleckchem, Houston, Tex. Information regarding these agents is also available at selleckchem.com.

As shown in Example 7, Torin significantly increased survival after infection with *Burkholderia cepacia* at two concentrations. It would be expected that these other TORC1/TORC2 inhibitors would have the same effect.

Additional agents for TORC2 inhibition would include those that inhibit gene expression of TORC2 components including Rictor, Sin1 and PROTOR components of TORC2. Inhibiting these components as well as activating mLST8 would specifically inhibit TORC2.

Means for inhibiting gene expression using short RNA molecules, for example, are known. Among these are short interfering RNA (siRNA), small temporal RNAs (stRNAs), short hairpin RNA (shRNA), and micro-RNAs (miRNAs). Short interfering RNAs silence genes through an mRNA degradation pathway, while stRNAs and miRNAs are approximately 21 or 22 nt RNAs that are processed from endogenously encoded hairpin-structured precursors, and function to silence genes via translational repression. See, e.g., McManus et al. (2002). *RNA* 8(6):842-50; Morris et al. (2004). *Science* 305(5688):1289-92; He and Hannon. (2004). *Nat. Rev. Genet.* 5(7):522-31.

"RNA interference, or RNAi" a form of post-transcriptional gene silencing ("PTGS"), describes effects that result from the introduction of double-stranded RNA into cells (reviewed in Fire. (1999). *Trends Genet.* 15:358-363; Sharp. (1999) *Genes Dev.* 13:139-141; Hunter. (1999). *Curr. Biol.* 9:R440-R442; Baulcombe. (1999). *Curr. Biol.* 9:R599-R601; Vaucheret et al. (1998). *Plant J.* 16:651-659). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. (2001). *Nature* 411:494-498). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of TORC2, siRNAs to the gene encoding the Rictor, Sin, and PROTOR components of TORC2 can be specifically designed using computer programs. Illustrative nucleotide sequences encoding the amino acid sequences of these components are readily available.

Software programs for predicting siRNA sequences to inhibit the expression of a target protein are commercially available and find use. One program, siDESIGN from Dharmacon, Inc. (Lafayette, Colo.), permits predicting siRNAs for any nucleic acid sequence, and is available on the internet at dharmacon.com. Programs for designing siRNAs are also available from others, including Genscript (available on the internet at genscript.com/ssl-bin/app/rnai) and, to academic and non-profit researchers, from the Whitehead Institute for Biomedical Research found on the worldwide web at "jura.wi.mitedu/pubint/http://iona.wi.mitedu/siR-NAext/."

Alternatively, double-stranded (ds) RNA is a powerful way of interfering with gene expression in a range of organisms that has recently been shown to be successful in mammals (Wianny and Zernicka-Goetz. (2002)., *Nat. Cell. Biol.* 2:70-75). Double stranded RNA corresponding to the sequences of a TORC2 component polynucleotides can be introduced into or expressed in oocytes and cells of a candidate organism to interfere with TORC2 activity.

Any suitable viral knockdown system could be utilized for decreasing TORC2 component mRNA levels including AAV, lentiviral vectors, or other suitable vectors.

Additionally, specifically targeted delivery of shRNA or other TORC2 blocking molecule (nucleic acid, peptide, or small molecule) could be delivered by targeted liposome, nanoparticle or other suitable means.

An approach for therapy of such disorders is to express anti-sense constructs directed against the polynucleotides of the components of TORC2 as described herein to inhibit gene function and to treat and/or prevent infection caused by a microbe as well as increasing immunity to an infection caused by a microbe.

Anti-sense constructs may be used to inhibit TORC2 to treat and/or prevent infection by a microbe and/or increase immunity to an infection by an antisense constructs, i.e., nucleic acid, such as RNA, constructs complementary to the sense nucleic acid or mRNA, are described in detail in U.S. Pat. No. 6,100,090.

Alternatively, gene therapy may be employed to control the endogenous production of the TORC2 components by the relevant cells in the subject. For example, a polynucleotide encoding a Rictor, Sin1 or PROTOR siRNA or a portion of this may be engineered for expression in a replication defective retroviral vector, as discussed below. The retroviral expression construct may then be isolated and introduced into a packaging cell transduced with a retroviral plasmid vector containing RNA encoding an siRNA such that the packaging cell now produces infectious viral particles containing the sequence of interest. These producer cells may be administered to a subject for engineering cells in vivo and regulating expression of the TORC2 component polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

MicroRNA can also be used to inhibit TORC2. MicroRNAs are small non-coding RNAs averaging 22 nucleotides that regulate the expression of their target mRNA transcripts by binding. Binding of microRNAs to their targets is specified by complementary base pairing between positions 2-8 of the microRNA and the target 3' untranslated region (3' UTR), an mRNA component that influences translation, stability and localization. MicroRNA-153 has been shown to target the Rictor component of TORC2 (Cui et al. 2016). Other microRNAs shown to inhibit TORC2 include miR-7, miR-99, miR-100, miR-101, miR-199a-3p, and miR-218 (Uesugi et al. 2011). Other such microRNA can be designed using the known sequence of the 3'UTR of Rictor, Sin, and PROTOR. Additionally, this microRNA can also be modified for increasing other desirable properties, such as increased stability, decreased degradation in the body, and increased cellular uptake.

Other agents would include antibodies to the components of TORC2. Such antibodies are commercially available or can be produced by methods known in the art.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies and humanized antibodies are particularly useful in the present invention.

Antibody fragments that have specific binding affinity for a target of interest can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments recognizing a target of interest can be produced through standard techniques, such as those disclosed in U.S. Pat. No. 4,946,778.

Per Inhibition

As shown herein, inhibition of the circadian regulator Period protein Per (such as found in the circadian mutants used in the experimental examples) increased survival, immunity and tolerance after infection by bacteria. Thus, one embodiment of the present invention is a method of increasing immunity and survival after infection in a subject by administering a therapeutically effective amount of an agent that inhibits Per.

Agents for use in the current invention include those known now and those developed in the future.

One preferred agent for Per inhibition would be a small molecule.

A further agent for Per inhibition would include those that inhibit gene expression of Per and include siRNA, stRNA, shRNA, and miRNA as discussed with regard to TORC2 inhibition.

Antibodies to Per can also be used in the methods of the invention.

Pharmaceutical Compositions and Methods of Administration

The present invention encompasses the administration of a TORC2 inhibitor, in some embodiments a small molecule. Preferred methods of administration include oral; mucosal, such as nasal, sublingual, vaginal, buccal, or rectal; parenteral, such as subcutaneous, intravenous, bolus injection, intramuscular, or intra-arterial; or transdermal administration to a subject. Thus, the TORC2 or Per inhibitor must be in the appropriate form for administration of choice.

Such compositions for administration may comprise a therapeutically effective amount of the serotonin inhibitor and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

These compositions can take the form of solutions, suspensions, emulsions, tablets, pills, capsules, powders, sustained-release formulations, cachets, troches, lozenges, dispersions, suppositories, ointments, cataplasms (poultices), pastes, powders, dressings, creams, plasters, patches, aerosols, gels, liquid dosage forms suitable for parenteral administration to a patient, and sterile solids (e.g., crystalline or amorphous solids) that can be reconstituted to provide liquid dosage forms suitable for parenteral administration to a patient. Such compositions will contain a therapeutically effective amount of the compound, preferably in purified form, together with a suitable form of carrier so as to provide the form for proper administration to the patient. The formulation should suit the mode of administration.

Pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient over a prolonged period of time.

Pharmaceutical compositions adapted for nasal and pulmonary administration may comprise solid carriers such as powders which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Selection of a therapeutically effective dose will be determined by the skilled artisan considering several factors which will be known to one of ordinary skill in the art. Such factors include the particular form of the inhibitor, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

When the TORC2 or Per inhibitor is a nucleic acid such as DNA, RNA, interfering RNA or microRNA, methods for delivery include receptor mediated endocytosis where the RNA is coupled to a targeting molecule that can bind to a specific cell surface receptor, inducing endocytosis and transfer of the RNA into cells. Coupling is normally achieved by covalently linking poly-lysine to the receptor molecule and then arranging for (reversible) binding of the negatively charged RNA to the positively charged poly-lysine component. Another approach utilizes the transferrin receptor or folate receptor which is expressed in many cell types. When producing the microRNA for this method of administration, the microRNA could be manufactured to have a guide strand which is identical to the microRNA of interest and a passenger strand that is modified and linked to a molecule for increasing cellular uptake Another method to administer the RNA to the proper tissue is direct injection/particle bombardment, where the RNA is be injected directly with a syringe and needle into a specific tissue, such as muscle.

An alternative direct injection approach uses particle bombardment ('gene gun') techniques: RNA is coated on to metal pellets and fired from a special gun into cells. Successful gene transfer into a number of different tissues has been obtained using this approach. Such direct injection techniques are simple and comparatively safe.

Another method for delivery of RNA to the proper tissue or cell is by using adeno-associated viruses (AAV). RNA delivered in these viral vectors is continually expressed, replacing the expression of the RNA that is not expressed in the subject. Also, AAV have different serotypes allowing for tissue-specific delivery due to the natural tropism toward different organs of each individual AAV serotype as well as the different cellular receptors with which each AAV serotype interacts. The use of tissue-specific promoters for expression allows for further specificity in addition to the AAV serotype.

Other mammalian virus vectors that can be used to deliver the RNA include oncoretroviral vectors, adenovirus vectors, Herpes simplex virus vectors, and lentiviruses.

Liposomes are spherical vesicles composed of synthetic lipid bilayers which mimic the structure of biological membranes. The RNA to be transferred is packaged in vitro with the liposomes and used directly for transferring the RNA to a suitable target tissue in vivo. The lipid coating allows the RNA to survive in vivo, bind to cells and be endocytosed into the cells. Cationic liposomes (where the positive charge on liposomes stabilize binding of negatively charged DNA), have are one type of liposome.

The RNAs can also be administered with a lipid to increase cellular uptake. The RNA may be administered in combination with a cationic lipid, including but not limited to, lipofectin, DOTMA, DOPE, and DOTAP.

Other lipid, or liposomal formulations including nanoparticles and methods of administration have been described as for example in U.S. Patent Publication 2003/0203865, 2002/0150626, 2003/0032615, and 2004/0048787. Methods used for forming particles are also disclosed, in U.S. Pat. Nos. 5,844,107, 5,877,302, 6,008,336, 6,077,835, 5,972,901, 6,200,801, and 5,972,900.

Subjects Benefitting from the Inhibition of TORC2 or Per

It has been discovered that the inhibition of TORC2 greatly increases survival after infection by bacteria, in particular *Burkholderia cepacia*. It has also been discovered that inhibition of Per increases survival after infection by bacteria.

*Burkholderia cepacia* is a gram-negative bacterium that is an opportunistic human pathogen that causes pneumonia in immunocompromised subjects, such as those with underlying lung disease such as cystic fibrosis or bronchiectasis. Additionally *Burkholderia cepacia* can cause central venous catheter-related infections in patients with cancer and on dialysis. *Burkholderia cepacia* also can colonize in fluids used in hospitals. Skin and soft-tissue infections, surgical-wound infections, and genitourinary tract infections with *B. cepacia* have also been reported. Mortality can be high from these infections especially in the immunocompromised.

Additionally, sepsis can occur from these bacterial infections especially in the immunocompromised and those being hospitalized or with devices such as catheters or those on dialysis.

Infection such as sepsis caused by other gram-negative bacteria can also be prevented and treated by the methods and compositions of the invention. These bacteria include but are not limited to *Acinetobacter baumannii, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis,* and *Salmonella typhi*.

Other bacterial infections, especially those that include a metabolic component in pathogenesis, can also be prevented and treated by the methods and compositions of the invention. Therapeutics that increase host tolerance of infection rather than target the clearance or containment of specific types of bacteria are predicted to be generally effective for multiple types of infection, rather than being bacteria-specific.

Thus, subjects who would benefit from administration of a TORC2 inhibitor or a Per inhibitor would be those diagnosed with a bacterial infection, including but not limited to *Burkholderia cepacia* or another gram-negative bacteria as well as other bacteria. Also subjects who would benefit from the administration of a TORC2 inhibitor or a Per inhibitor would be those diagnosed with sepsis or septicemia.

Additionally subjects who are at risk for bacterial infections would also benefit from the administration of a TORC2 inhibitor or a Per inhibitor. Those subjects would include immunocompromised subjects, especially those with an underlying lung disease, or a subject receiving fluids such as through dialysis, and subjects who are being hospitalized.

Kits

The present invention also provides kits comprising the components of the combinations of the invention in kit form. A kit of the present invention includes one or more components including, but not limited to, the viral vectors, RNAi, shRNA or other TORC2 inhibitors or Per inhibitors, as discussed herein, in association with one or more additional components including, but not limited to a pharmaceutically acceptable carrier. The viral vectors, RNAi, shRNA or other TORC2 or Per inhibitors, composition and/or the therapeutic agent can be formulated as a pure composition or in combination with a pharmaceutically acceptable carrier, in a pharmaceutical composition.

In one embodiment, a kit includes the viral vectors, RNAi, shRNA, or other TORC2 inhibitors, of the invention or a pharmaceutical composition thereof in one container (e.g., in a sterile glass or plastic vial).

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, and proper storage conditions,

EXAMPLES

The present invention may be better understood by reference to the following non-limiting examples, which are presented in order to more fully illustrate the preferred embodiments of the invention. They should in no way be construed to limit the broad scope of the invention.

Example 1—Materials and Methods

Fly Strains $w^{1118}per^{01}$ (null) mutants (Konopka and Benzer 1971) were outcrossed with a $w^{1118}$ Canton S strain, used as isogenic controls (Krishnan et al. 2008). Wild-type Oregon R flies were used to test effects of dietary components and rapamycin. UAS-Tsc1/Tsc2 (from Marc Tatar) (Tapon et al. 2001) homozygous males were crossed to $w^{1118}$; tub>Gal80-ts; tub>Gal4/TM6c virgins and maintained at 18° C. until 29° C. transgene induction 24 or 48 hours before infection.

rictor null mutants (imprecise p-element excision alleles $rictor^{\Delta 1}$ and $rictor^{\Delta 2}$) and precise excision controls were obtained from Stephen Cohen (Dimitroff et al. 2012). Experiments used hemizygous $rictor^{\Delta 2}$ flies.

$Sin1^{e03756}$ (SAPK-interacting protein 1) mutants are null piggyBac transposon insertion mutants from Bloomington Drosophila Stock Center, stock #18188 (Hietakangas and Cohen 2007). 5-10 day-old males raised on standard molasses food were used for all experiments.

Infections

Infections were performed as previously described (Schneider et al. 2007) with Burkholderia cepacia (ATCC strain #25416). Death was assayed visually the next day every hour or more frequently as needed. Survival curves are plotted as Kaplan-Meier graphs and log-rank analysis performed using GraphPad Prism. All infection experiments were performed with a minimum of 3 independent trials and yielded statistically similar results, except where noted. Graphs and p-values in figures are representative trials.

Bacterial Load Quantitation

Bacterial load was quantified as described (Pham et al. 2007) and analyzed by unpaired t-tests for 0 hour time points; subsequent time points were analyzed with non-parametric Mann-Whitney tests, which do not assume normal distribution as bacteria grow exponentially. Data are plotted with SEM.

qRT-PCR, Melanization, and Phagocytosis Assays

Assays were performed as described, using B. cepacia for infection (Stone et al. 2012; Schwager et al. 2013). p-values for AMP induction and melanization were obtained by t-tests for three independent trials; data are represented as mean±SEM. p-values for phagocytosis assays were obtained by log-rank analysis.

Primers used for determination of antimicrobial peptide (AMP) induction were as follows:

```
Dipt
                                       (SEQ ID NO 1)
    Left Primer CCGCAGTACCCACTCAATC (SEQ ID NO: 2)
    Right Primer CCCAAGTGCTGTCCATATCC Dro
                                      (SEQ ID NO: 3)
    Left Primer CCATCGAGGATCACCTGACT (SEQ ID NO: 4)
    Right Primer CTTTAGGCGGGCAGAATG
```

Protein Extraction and Western Blotting

Western blot analysis of whole-fly homogenates was performed by standard methods using 1:1000 anti-phospho-S6K (Thr398) (Cell Signaling #9209), 1:10,000 anti-Actin-HRP (Sigma A3854), and 1:2000 anti-rabbit-HRP (Cell Signaling #7074). p-values were obtained by unpaired t-test; data are represented as mean±SEM.

Example 2—Period ($Per^{01}$) Mutants are More Tolerant of Infection than Wild Type Flies Arrhythmic $per^{01}$ Drosophila mutants survived longer than isogenic wild type controls when infected with the human pathogen Burkholderia cepacia, a previously described infection model (Castonguay-Vanier et al. 2010; D'Argenio et al. 2001; Schneider et al. 2007; Schwager et al. 2013) (FIGS. 1A and 1B, p<0.0001).

To determine whether this increased survival was due to altered resistance or tolerance, bacterial loads of individual flies during infection were measured. Whether the kinetics of survival were slow (over days, 18° C.) or fast (over hours, 29° C.), wild type and $per^{01}$ mutants carried equivalent bacterial loads (FIGS. 1C and 1D, p>0.05 for each time point). This result suggests that the enhanced survival of $per^{01}$ mutants is not due to greater resistance, but due to greater host tolerance.

This was confirmed by the analysis of three well-characterized resistance mechanisms following infection: antimicrobial peptide (AMP) induction, melanization, and phagocytosis. No significant differences were found between wild type and $per^{01}$ mutants in B. cepacia-induced antimicrobial peptide or AMP expression via the Toll pathway as shown by Drosomycin and via the imd pathway as shown Diptericin (FIGS. 1E and 1F). The same results were found with other AMPs such as Attacin, Cecropin, Defensin, Drosocin and Metchnikowin (results not shown).

There was no significant differences were found between wild type and $per^{01}$ mutants in melanization, wound site or systemic, typically not induced by B. cepacia (FIG. 1G) (Ayres and Schneider 2008).

While inhibition of phagocytosis by bead pre-injection decreased survival of both $per^{01}$ and wild type controls (both p<0.0001), $per^{01}$ mutants still survived significantly longer than wild type (FIG. 1H, p<0.0001), suggesting that phagocytosis is not responsible for the increased survival of per$^{01}$ mutants.

Taken together, these results suggest that per$^{01}$ mutants have increased tolerance, not resistance, during *B. cepacia* infection.

Example 3—Dietary Glucose and Amino Acids Enhance Infection Tolerance in Wild Type Flies It was shown that the increased survival of the per$^{01}$ mutants was due to increased feeding and that a restrictive diet of only water, agar, and 1% glucose decreased survival and host tolerance of infection in both the mutants and wild type flies (results not shown).

To identify specific dietary components contributing to tolerance of infection, a restricted diet was supplemented with defined nutrients. Because per$^{01}$ mutants display pleiotropic defects in metabolism and other circadian-regulated physiologies, wild type flies were used.

Figure 2B:
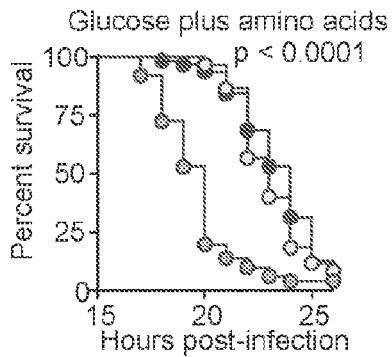
FIG. 2B shows percent survival of infected flies fed 5% glucose with amino acids (n=60) relative to standard food and 5% glucose alone (n=51, p<0.0001 in all cases); the diet of glucose plus amino acids was sufficient to cause survival kinetics similar to standard food (n=64, n.s.).
Figure 2C:
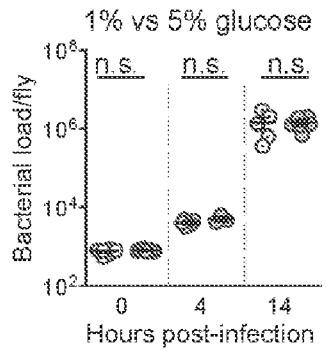
FIG. 2C shows the bacterial load comparisons for flies fed 1% vs. 5% glucose (n=6 flies/time point, n.s. for all).

To determine if increasing dietary glucose complements the restricted diet, which contains 1% glucose, the effects of titrating dietary glucose (1%, 5%, 10%, or 15% glucose, no protein) with standard food (5-10% sugar, plus yeast extract) was compared. Wild type flies exhibited shortest survival time when switched to 1% dietary glucose 24 hours before infection and survived longest on standard food (FIG. 2A, p<0.0001 comparing standard food or 1% glucose with any other condition). While increasing dietary glucose from 1% to 5% increased survival time (FIG. 2A, p<0.0001), further increases in dietary glucose did not (FIG. 2A, p>0.05 for any pair-wise comparison of 5%, 10%, and 15% glucose). Despite the survival benefit conferred by 5% glucose relative to 1% glucose, bacterial load was unchanged (FIG. 2C, p>0.05 for all time points). Moreover, no glucose-only diets increased survival time to that observed on standard food (p<0.0001). Thus, glucose enhances infection tolerance, but glucose alone is not sufficient for optimal survival of infection. This result suggests that other components in standard food also contribute to survival of *B. cepacia* infection.

Figure 2D:
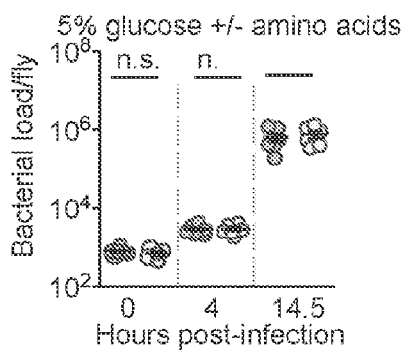
FIG. 2D shows bacterial load comparisons for flies fed 5% glucose vs. 5% glucose plus amino acids (n=6 flies/time 24 point, n.s. for all).

In addition to sugar, standard food contains a complex mixture of lipids, proteins, vitamins, and other nutrients derived from yeast and cornmeal ingredients. It was tested whether 5% glucose supplemented with amino acids was sufficient to substitute for standard food. A diet of 5% glucose plus amino acids 24 hours before infection significantly increased survival time relative to 5% glucose alone (FIG. 2B, p<0.0001), with no change in bacterial load (FIG. 2D, all time points p>0.05). In fact, 5% glucose plus amino acids was sufficient to increase survival time to that observed with standard food (FIG. 2B, p>0.05). The survival benefit of amino acids was not dependent on high glucose and was also observed with 1% glucose diet (results not shown). Thus, both dietary glucose and amino acids contribute to tolerance of infection, and acute exposure to both nutrients approximately 24 hours before *B. cepacia* infection is necessary for optimal survival.

Figure 2E:
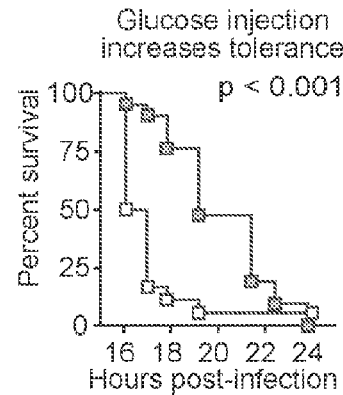
FIG. 2E shows percent survival of flies injected 1.5 hours before infection with 50 nL of 5% glucose (n=21) and with PBS control (n=18, p=0.0007).

Additionally, it was found that glucose was required at the time of infection for increased host tolerance. A 50 nL injection of 5% glucose administered into the circulatory system of diet-restricted flies could significantly increase infection survival time relative to buffer injection (FIG. 2E, p=0.0007). This dose of glucose is equivalent to the quantity ingested by a single fly in 1 hour (calculated from feeding experiments). Glucose injection most often promoted survival when administered within 2 hours before or at the time of infection (FIG. 2E, 5/8 experiments). In contrast, glucose injected more than 2 hours before infection or after infection rarely provided any survival benefit (results not shown). Thus, with the experimental infection protocol, the effective time window for glucose-induced survival is unexpectedly narrow, consistent with an acute rather than chronic effect of diet upon infection tolerance.

Figure 2F:
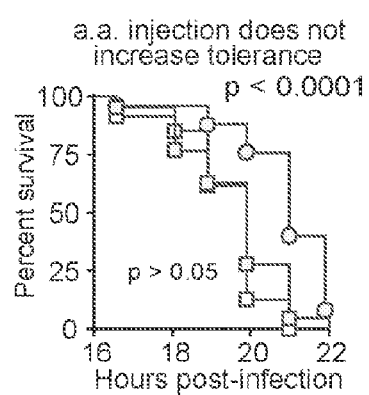
FIG. 2F shows percent survival of flies injected with amino acids prior to infection (n=43) and with PBS control (n=25, p<0.0001). p-values for survival curve comparisons were obtained by log-rank analysis; p-values for bacterial load comparisons were obtained by unpaired t-test (0 h) and non-parametric Mann-Whitney test (later time points). n.s.=not significant (p>0.05).

These results suggest that acute glucose intake stimulates specific signaling pathways that increase immune tolerance when activated around the time of infection. Injection of amino acids at two different concentrations at different time points before or during infection did not improve survival time (FIG. 2F amino acids vs. buffer injection, p>0.05). Flies injected with buffer were still able to respond to dietary amino acids (FIG. 2F, p<0.0001). Thus, in contrast to glucose, amino acids appear to stimulate infection tolerance only when ingested and not when injected.

Example 4—Increased TORC1 Signaling is Correlated with Increased Survival for Per$^{01}$ Mutants and Flies with Greater Nutrient Availability Since transient exposure to nutrients enhances infection tolerance, it was next determined whether molecular pathways stimulated by these nutrients play a role in survival of *B. cepacia* infection. The role of insulin-like signaling during infection has been characterized in *Drosophila*. Thus, the less well characterized role of the kinase TOR in innate immunity was focused on, as TOR complex 1 (TORC1) is the canonical sensor of amino acid availability (Krishnan et al. 2008).

Figure 3H:
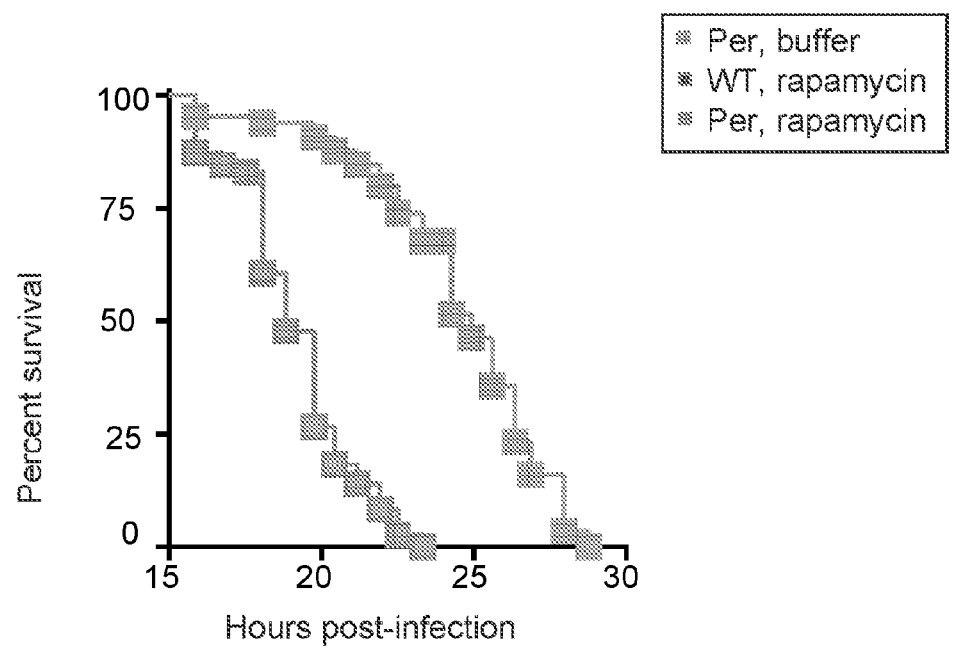
FIG. 3H shows percent survival of per$^{01}$ mutants injected with rapamycin versus a vehicle control. Rapamycin injection decreases survival of per$^{01}$ mutants relative to vehicle alone (n=71, n=65; p<0.0001).

First it was determined if TORC1 kinase activity is circadian-regulated by monitoring phosphorylation of its downstream target S6K (Martin and Mohr 2000) over the circadian cycle in wild type and per$^{01}$ mutants. It was found that TORC1 activity oscillated over the circadian cycle in wild type flies, with a peak of activity at Zeitgeber time (ZT) ZT9-13 (FIG. 3A). This peak of TORC1 activity correlated with low per protein levels in wild type (Khapre et al. 2014). Consistent with this, TORC1 activity did not oscillate in per$^{01}$ mutants and the mutants exhibited high, equivalent levels at both ZT9 and ZT21 (FIG. 3B). Thus, TORC1 activation is circadian-regulated and increased in per$^{01}$ mutants during the time course of infection, suggesting that increased TORC1 activation may contribute to pee mutants' increased survival of infection.

TORC1 activity of wild type flies in dietary conditions associated with increased survival of infection was tested. It was found that TORC1 activity was higher in flies fed food containing amino acids than in flies fed food without amino acids. The nutrients activated TORC1 signaling, as evidenced by increased levels of phospho-S6K (FIG. 3C, all p≤0.0163). Thus, both wild type flies on nutrient-rich diets and per$^{01}$ mutants exhibited increased TORC1 kinase activity. Interestingly, TORC1 activity was higher in flies fed 5% glucose plus amino acids than those fed standard food (p=0.0014), suggesting that TORC1 activity may not solely mediate differences in survival.

Example 5—Decreased TORC1 Signaling Causes Decreased Resistance

To directly test the role of TORC1 in survival of infection, TORC1 activity was inhibited in two ways. First, flies were injected with rapamycin, a TORC1-specific inhibitor (9.6 ng per fly, equivalent to the mammalian dose of 16 mg/kg (Lee et al. 2009; Loeweth et al. 2002)). Injection of rapamycin inhibited survival of infection relative to injection of buffer alone (FIG. 3D, p<0.0001).

Unexpectedly, it was found that rapamycin-injected flies had increased bacterial load, indicating decreased resistance (FIG. 5E, p>0.05, p=0.0049, p=0.0198).

Second, TORC1 activity was inhibited using a temperature-driven system to over-express Tsc1 and Tsc2, proteins forming a TORC1-inhibitory complex (Huang and Manning 2008). Tsc1/2 over-expression was confirmed by qRT-PCR (results not shown). Similar to rapamycin injection, genetic inhibition of TORC1 reduced survival after *B. cepacia* infection (FIG. 3F, p<0.0001 for both controls) and caused increased bacterial loads (FIG. 3G, p>0.05, p=0.0367, p=0.0022).

Taken together, these results suggest that in flies, as in vertebrates, TORC1 mediates resistance against *B. cepacia* infection (Foldenauer et al. 2013).

Figure 3I:
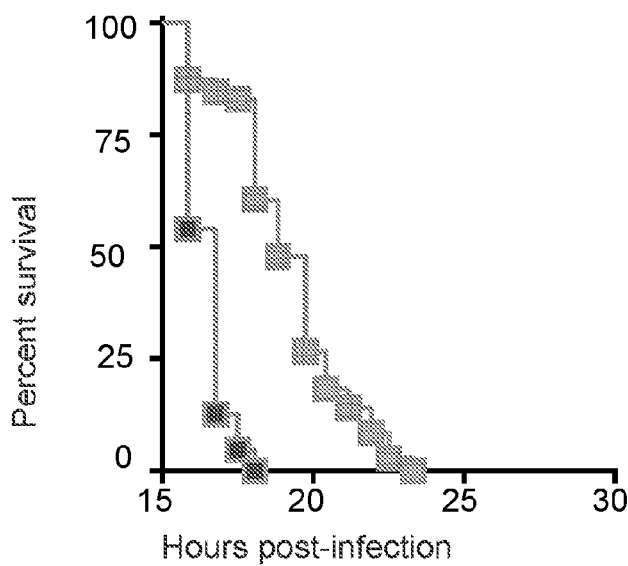
FIG. 3I shows percent survival of per$^{01}$ mutants injected with rapamycin versus wild type injected with rapamycin. When injected with rapamycin, per$^{01}$ mutants survive longer than wild type (n=71, n=63; p<0.0001). p-values for survival curve comparisons were obtained by log-rank analysis; p-values for bacterial load comparisons were obtained using unpaired t tests for 0 hour time points, while subsequent time points were tested with non-parametric Mann-Whitney U tests. n.s.=not significant (p>0.05). *=p≤0.05; =p≤0.01; *=p≤0.001.

While inhibition of TORC1 in per$^{01}$ mutants by rapamycin injection decreased their survival after infection (FIG. 3H), rapamycin injection did not abolish per$^{01}$ mutants' survival advantage over wild-type controls (FIG. 3I), suggesting that increased TORC1 activity is not solely responsible for their increased survival. Rapamycin injection decreases survival of per$^{01}$ mutants relative to buffer alone (n=71, n=65; p<0.0001), suggesting that per is upstream, rather than downstream, of TORC1 in this context.

Example 6—Increased Resistance was Correlated with Decreased TORC2 Signaling

TOR kinase associates with another, less well-understood complex, TORC2. Since TORC1 and TORC2 might compete for limited TOR kinase and these complexes appear to have opposing roles in cell growth and T cell differentiation (Ikai et al. 2011; Delgoffe et al. 2009), it was next asked whether TORC2 activity underlies infection tolerance. TORC2 is not known to play a role in survival of infection.

To test this, TORC2 signaling was reduced in two ways.

Figure 4A:
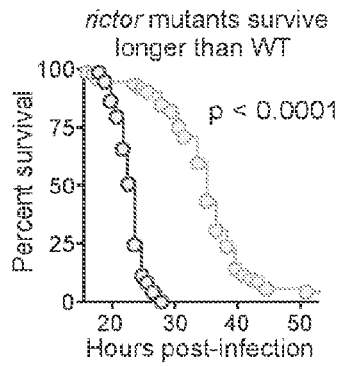
FIG. 4A shows percent survival of rictor$^{Δ2}$ mutants (n=72) and wild type (n=73) after infection (n=73, p<0.0001).
Figure 4B:
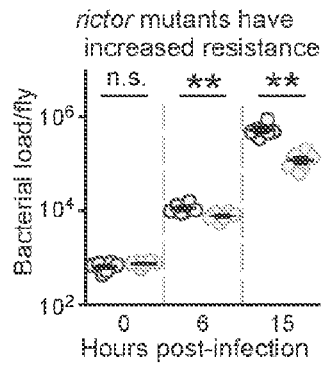
FIG. 4B shows bacterial load after infection of rictor$^{Δ2}$ mutants and wild type (n=6, all groups, 0 hr n.s., 6 hrs p=0.0087, 15 hrs p=0.0022).

First, the survival of mutants lacking Rictor, an essential molecular component of TORC2 but not TORC1, was examined after *B. cepacia* infection. rictor$^{\Delta 2}$ mutants had the opposite survival phenotype as that seen with TORC1 inhibition: they lived dramatically longer than isogenic controls (FIG. 4A, p<0.0001). It was also found that rictor$^{\Delta 2}$ mutants carried decreased bacterial load relative to wild type (FIG. 4B, p>0.05, p=0.0087, p=0.0022). These results suggest that, while TORC1 activates resistance, TORC2 inhibits resistance.

Figure 4C:
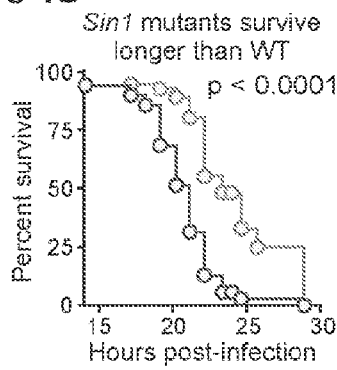
FIG. 4C shows percent survival of Sin1 mutants (n=56) and wild type after infection (n=70, p<0.0001).
Figure 4D:
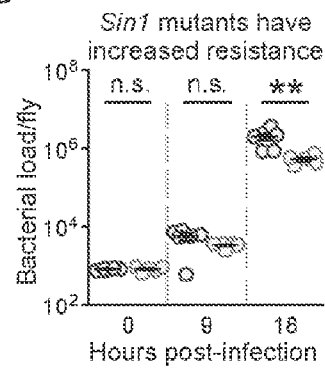
FIG. 4D shows bacterial load comparisons of Sin1 mutants and wild type after infection (n=6, all groups, 0 hr n.s., 9 hrs n.s., 18 hrs p=0.0043).

To confirm this, mutants lacking Sin1, another TORC2-specific component, were examined Similar to rictor$^{\Delta 2}$ mutants, Sin1$^{e03756}$ mutants exhibited increased survival time after infection and decreased bacterial load relative to wild type (FIG. 4C, p<0.0001, FIG. 4D, p>0.05, p>0.05, p=0.0043). Thus, inhibition of TORC2 by loss of either Rictor or Sin1 increased both survival and resistance against *B. cepacia* infection.

Figure 4E:
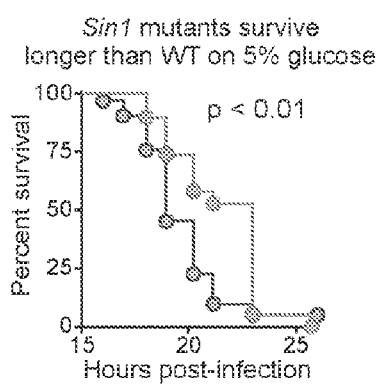
FIG. 4E shows percent survival of Sin1 mutants (n=24) and wild type flies after infection in the absence of dietary amino acids (5% glucose alone (n=19, p=0.0051).
Figure 4F:
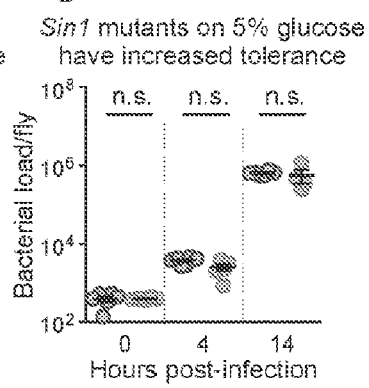
FIG. 4F shows bacterial load for Sin1 mutants and wild type after infection in the absence of dietary amino acids (5% glucose alone).
Figure 4G:
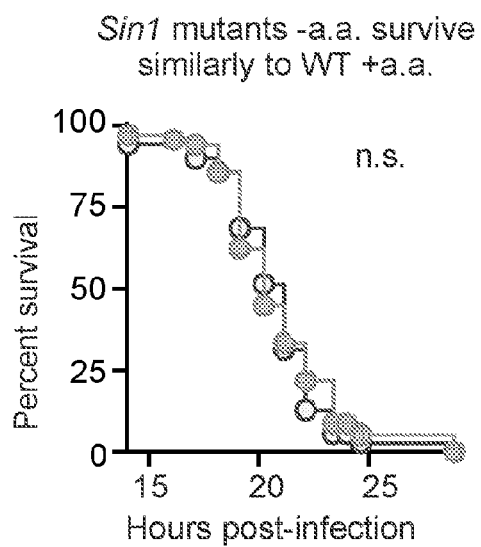
FIG. 4G shows percent survival of Sin1 mutants deprived of amino acids (n=69) and wild type fed amino acids (n=70, n.s.).
Figure 4H:
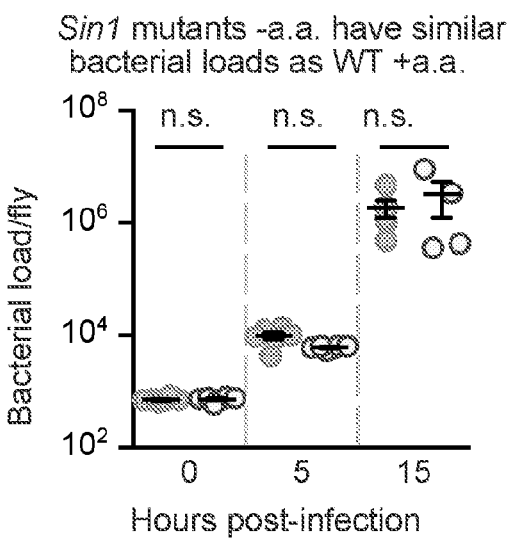
FIG. 4H shows bacterial load comparisons for Sin1 mutants deprived of amino acids and wild type fed amino acids. p-values for survival curve comparisons were obtained by log-rank analysis; p-values for bacterial load comparisons were obtained using unpaired t-tests for 0 hour time points, while subsequent time points were tested with non-parametric Mann-Whitney U tests. n.s.=not significant (p>0.05); **=p<0.01.

Because increased tolerance is defined functionally as increased survival without decreased bacterial load, increased resistance due to dietary TORC1 activation might mask increased tolerance due to genetic TORC2 inhibition. Thus, Sin1$^{e03756}$ mutants were tested for survival of infection and bacterial load in the absence of dietary amino acids. Consistent with TORC2 inhibition of tolerance, Sin1$^{e03756}$ mutants survived infection longer than wild type with no decrease in bacterial load (FIG. 4E, p=0.0051, FIG. 4F, all p>0.05). Interestingly, Sin1$^{e03756}$ mutants without amino acids had identical survival kinetics and bacterial load as wild type flies fed amino acids, suggesting that amino acids had an equivalent effect on tolerance as loss of Sin1 (FIGS. 4G and 4H). These results suggest that Sin1, an essential component of TORC2, inhibits both resistance and tolerance of *B. cepacia* infection.

Example 7—A TORC2 Inhibitor Significantly Increased Survival

Wild type flies, 5-7 day old males, were fed two different concentrations (250 μM and 500 μM) of Torin (MedChem Express), a TORC1 and TORC2 inhibitor, for two days prior to infection with *Burkholderia cepacia* as described in Example 1. Controls were fed a vehicle.

Figure 5A:
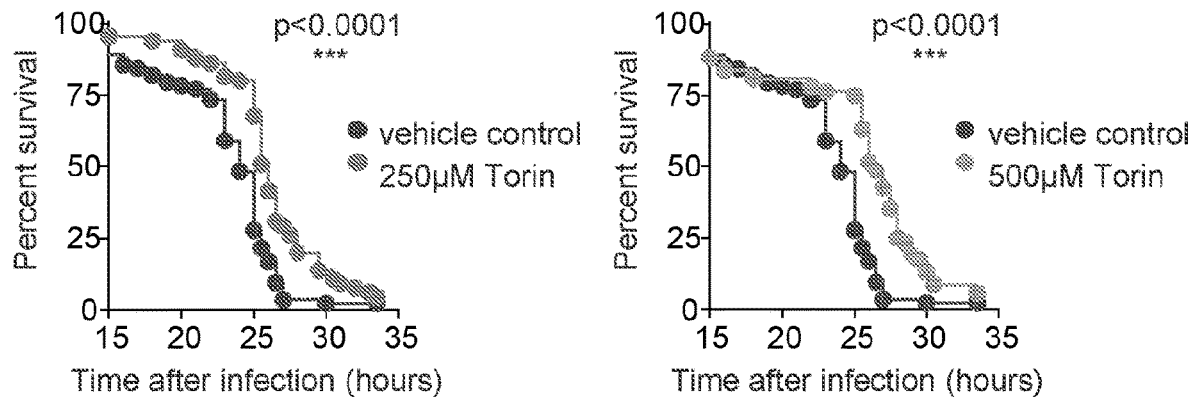
FIG. 5A are the graphs showing percent survival versus time of infection in hours of male wild type Drosophila fed Torin two days before infection with Burkholderia cepacia and controls fed a vehicle. The graph on the left show the results of flies fed 250 μM of Torin versus controls and the graph on the right shows the results of flies fed 500 μM of Torin versus controls. p<0.0001 for both concentrations of Torin relative to vehicle-fed.

As shown in FIG. 5A, relative to vehicle-fed controls, survival of infection was significantly increased for both concentrations (p<0.0001). This is likely due to TORC2 inhibition as TORC1 inhibition (e.g., by rapamycin and genetic manipulation) would decrease survival of infection.

Figure 5B:
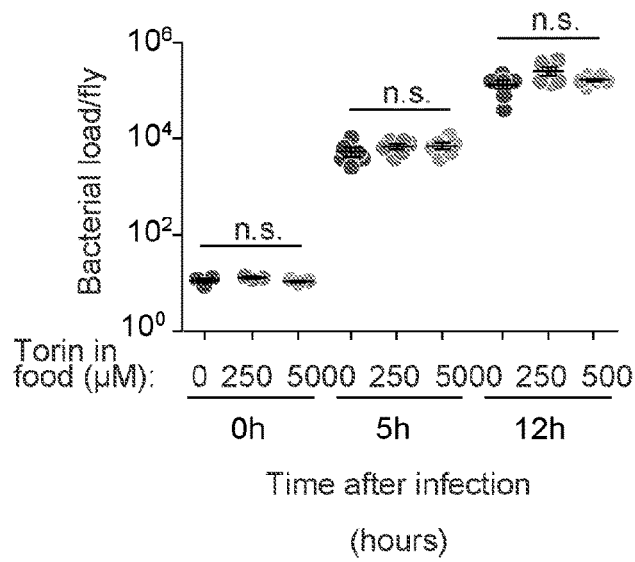
FIG. 5B shows the bacterial load of the flies. n.s.=not significant, p>0.05. n=60 flies per genotype for survival curves, 6 per genotype per timepoint for bacterial load quantification. p-values were obtained by log-rank analysis for survival curves and by Mann-Whitney test for bacterial loads.

As shown in FIG. 5B, the flies that were fed Torin, while they survived infection longer than the vehicle-fed flies, there was not significant change in bacterial load.

REFERENCES

AlQurashi et al. (2013) Chemical Inhibitors and microRNAs (miRNA) Targeting the Mammalian Target of Rapamycin (mTOR) Pathway: Potential for Novel Anticancer Therapeutics. *Int. J. Mol. Sci.* 14:3874-3900.

Ayres et al. (2008). Identification of *Drosophila* mutants altering defense of and endurance to *Listeria monocytogenes* infection. *Genetics* 178:1807-1815.

Ayres and Schneider. (2009). The role of anorexia in resistance and tolerance to infections in *Drosophila*. *PLoS Biol* 7:e1000150.

Ayres and Schneider. (2008). A signaling protease required for melanization in *Drosophila* affects resistance and tolerance of infections. *PLoS Biol* 6:2764-2773.

Brennan and Anderson. (2004). *Drosophila*: the genetics of innate immune recognition and response. *Annual Review of Immunology* 22:457-483.

Brown et al. (2011). Mammalian Target of Rapamycin Complex 2 (mTORC2) Negatively Regulates Toll-like Receptor 4-mediated Inflammatory Response via FoxO1. *Journal of Biological Chemistry* 286:44295-44305.

Castonguay-Vanier et al. (2010). *Drosophila melanogaster* as a model host for the *Burkholderia cepacia* complex. *PloS one* 5:e11467.

Cui et al. (2016). microRNA-153 targets mTORC2 component Rictor to inhibit glioma cells. *Plos One* 11:e0156915.

D'Argenio et al. (2001). *Drosophila* as a model host for *Pseudomonas aeruginosa* infection. *J Bacteriol*. 183:1466-1471.

Delgoffe et al. (2009). The mTOR Kinase Differentially Regulates Effector and Regulatory T Cell Lineage Commitment. *Immunity* 30:832-844.

Dimitroff et al. (2012). Diet and Energy-Sensing Inputs Affect TorC1-Mediated Axon Misrouting but Not TorC2-Directed Synapse Growth in a *Drosophila* Model of Tuberous Sclerosis. *PloS one* 7:e30722.

Dionne et al. (2006). Akt and FOXO dysregulation contribute to infection-induced wasting in *Drosophila*. *Current Biology* 16:1977-1985.

Foldenauer et al. (2013) Mammalian target of rapamycin regulates IL-10 and resistance to *Pseudomonas aeruginosa* corneal infection. *J. Immunol.* 190:5649-58

Foldenauer et al. (2013) Mammalian targets of rapamycin regulates IL-10 and resistance to *Pseudomonas aeruginosa* corneal infection. *J. Immunol.* 190:5949-58.

Green et al. (2008). The meter of metabolism. *Cell* 134:728-742.

Hietakangas and Cohen. (2007). Re-evaluating AKT regulation: role of TOR complex 2 in tissue growth. *Genes Dev* 21:632-637.

Huang and Manning (2008). The TSC1-TSC2 complex: a molecular switchboard controlling cell growth. *Biochemical Journal* 412:179-190.

Ikai et al. (2011). The reverse, but coordinated, roles of Tor2 (TORC1) and Tor1 (TORC2) kinases for growth, cell cycle and separase-mediated mitosis in *Schizosaccharomyces pombe. Open Biol.* 1:110007.

Khapre et al. (2014). Metabolic clock generates nutrient anticipation rhythms in mTOR signaling. *Aging* 6:675-689.

Konopka and Benzer (1971). Clock mutants of *Drosophila melanogaster. Proc. Natl. Acad. Sci.* 68:2112-2116.

Krishnan et al. (2008). Circadian regulation of response to oxidative stress in *Drosophila melanogaster. Biochem Biophys Res Commun* 374:299-303.

Lee et al. (2009) Rapamycin weekly maintenance dosing and the potential efficacy of combination sorafenib plus rapamycin but not atorvastatin or doxycycline in tuberous sclerosis preclinical models. *BMC Pharmacol.* 9:8.

Lee and Edery. (2008). Circadian regulation in the ability of *Drosophila* to combat pathogenic infections. *Current Biology* 18:195-199.

Loewith et al. (2002). Two TOR complexes, only one of which is rapamycin sensitive, have distinct roles in cell growth control. *Molecular Cell* 10:457-468.

Lowrey and Takahashi. (2004). Mammalian circadian biology: elucidating genome-wide levels of temporal organization. *Annu. Rev. Genomics Hum. Genet.* 5:407-441.

Martin and Mohr. (2000). Invasion and intracellular survival of *Burkholderia cepacia. Infect. Immun.* 68:24-29.

Medzhitov et al. (2012). Disease tolerance as a defense strategy. *Science* 335:936-941.

Pham et al. (2007). A specific primed immune response in *Drosophila* is dependent on phagocytes. *PLoS Pathog* 3:e26.

Raberg et al. (2007). Disentangling genetic variation for resistance and tolerance to infectious diseases in animals. *Science* 318:812-814.

Schneider et al. (2007). *Drosophila* eiger mutants are sensitive to extracellular pathogens. *PLoS Pathog.* 3:e41.

Schneider and Ayres. (2008). Two ways to survive infection: what resistance and tolerance can teach us about treating infectious diseases. *Nat. Rev. Immunol.* 8:889-895.

Schwager et al. (2013). Identification of *Burkholderia cenocepacia* Strain H111 Virulence Factors Using Nonmammalian Infection Hosts. *Infection and Immunity* 81:143-153.

Shirasu-Hiza et al. (2007). Interactions between circadian rhythm and immunity in *Drosophila melanogaster. Current Biology* 17: R353-355.

Sparks and Guertin. (2010) Targeting mTOR; prospects for mTOR complex 2 inhibitors in cancer therapy. *Oncogene* 29:3733-3744

Stone et al. (2012) The circadian clock protein timeless regulates phagocytosis of bacteria in *Drosophila. PLoS Pathog* 8:e1002445.

Tapon et al. (2001). The *Drosophila* tuberous sclerosis complex gene homologs restrict cell growth and cell proliferation. *Cell* 105, 345-355.

Thomson et al. (2009). Immunoregulatory functions of mTOR inhibition. *Nature Review Immunology* 9:324-337.

Uesugi et al. (2011) The tumor suppressive microRNA miR-218 targets the mTOR component Rictor and inhibits AKT phosphorylation in oral cancer. *Cancer Res.* 71:5765-78.

Xu et al. (2008). Regulation of feeding and metabolism by neuronal and peripheral clocks in *Drosophila. Cell Metabolism* 8:289-300.

The invention claimed is:

1. A method of increasing survival of an infection caused by *Burkholderia cepacia*, comprising administering to a subject in need thereof, a therapeutically effective amount of a small molecule that inhibits TOR complex 2, wherein the small molecule is chosen from the group consisting of Torin 1, Torin 2, torkinib (PP242), PP30, Ku-0063794, WAY-600, WYE-687, WYE-354, AZD8055, INK128, OS1027, AZD2014, omipalisib, wortmannin, LY294002, PI-103, BGT226, XL765, and NVP-BEZ235.

2. The method of claim 1, wherein the agent does not inhibit TOR complex 1.

3. A method of increasing survival and immunity to *Burkholderia cepacia*, comprising administering to a subject in need thereof, a therapeutically effective amount of an agent that inhibits TOR complex 2, wherein the agent is chosen from the group consisting of Torin 1, Torin 2, torkinib (PP242), PP30, Ku-0063794, WAY-600, WYE-687, WYE-354, AZD8055, INK128, OS1027, AZD2014, omipalisib, wortmannin, LY294002, PI-103, BGT226, XL765, and NVP-BEZ235.

4. The method of claim 3, wherein the agent does not inhibit TOR complex claim 1.

* * * * *